United States Patent [19]

Morel

[11] Patent Number: 4,460,786

[45] Date of Patent: Jul. 17, 1984

[54] PROCESS FOR THE SELECTIVE ADDITION OF A COMPOUND HAVING AN ACTIVATED CARBON ATOM ONTO A SUBSTITUTED CONJUGATED DIENE

[75] Inventor: Didier Morel, Lyons, France

[73] Assignee: Rhone-Poulenc Industries, Paris, France

[21] Appl. No.: 501,049

[22] Filed: Jun. 7, 1983

Related U.S. Application Data

[63] Continuation of Ser. No. 281,780, Jul. 9, 1981, abandoned.

[30] Foreign Application Priority Data

Jul. 10, 1980 [FR] France .................................. 80 15355
May 11, 1981 [FR] France .................................. 81 09322

[51] Int. Cl.$^3$ ...................... C07L 45/68; C07L 67/347
[52] U.S. Cl. ..................................... 560/126; 560/174; 568/31; 568/395
[58] Field of Search .................. 568/31, 395; 560/126, 560/174

[56] References Cited

U.S. PATENT DOCUMENTS 3,723,500  3/1973  Coulson ...................... 260/465.8 R
3,998,872  12/1976  Symon ................................. 260/483
4,142,060  2/1979  Kuntz ................................. 568/840

OTHER PUBLICATIONS

Baker et al., J. Chem. Soc. Perkin II, 1133, (1975).
Chemical Abstracts, 68 39012J; 69 10543T; 70 67626X, 106666G; 72 42700V, 54621H; 73 34822S, 120112S; 75 5169V, 98185K, 88070E; 76 99041T; 77 125885P; 80 37304E; 81 3379P; 82 124686R, 155389A; 84 165073Y; 83 10446C; 88 121457E, 136809V; 90 187131S.

Primary Examiner—Robert Gerstl
Attorney, Agent, or Firm—Stevens, Davis, Miller & Mosher

[57] ABSTRACT

The selective addition of a compound having an activated carbon atom onto the carbon atom in the 4-position of a buta-1,3-diene carrying a hydrocarbon substituent on the carbon atom in the 2-position is achieved by reacting the compound having the activated carbon atom with the buta-1,3-diene carrying the hydrocarbon substituent in water or in an aqueous-alcoholic mixture in the presence of a catalyst which consists of at least one water-soluble phosphine and at least one rhodium compound, the catalyst being in solution in the water or aqueous alcoholic mixture. The products obtained are useful as precursors of intermediates for the synthesis of vitamins and perfumes.

15 Claims, No Drawings

PROCESS FOR THE SELECTIVE ADDITION OF A COMPOUND HAVING AN ACTIVATED CARBON ATOM ONTO A SUBSTITUTED CONJUGATED DIENE

This application is a continuation of application Ser. No. 281,780, filed July 9, 1981 now abandoned.

The present invention relates to a process for the selective addition of a compound having an activated carbon atom onto a conjugated diene and to novel compounds and mixtures thereby produced.

French Patent Specification No. 2,366,237 and the corresponding U.K. Patent Specification No. 1,553,002 (Rhone-Poulenc Industries, inventor E. Kuntz) describe the reaction of at least one mol of diene with a compound having a labile hydrogen. Reaction is carried out in the presence of a catalyst which consists, on the one hand, of a water-soluble phosphine, and, on the other hand, of a transition metal (in the form of the metal or in the form of a compound). Water is introduced into the reaction medium and the catalyst dissolves in the water. The transition metal is preferably chosen from palladium, nickel, platinum, cobalt and rhodium, palladium being particularly preferred metal. It is specified that, if one mol of diene, for example butadiene, is reacted with one mol of a compound XH having a labile hydrogen, the following compounds are mainly obtained:

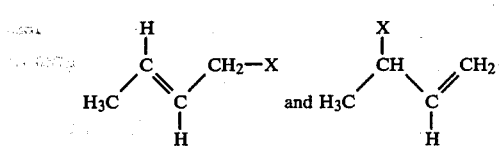

Pursuing this research, I have focused work on the preparation of the compounds resulting from the addition of a compound having an activated carbon atom, of the formula:

in which one of Y and Z is an electron-attracting group and the other represents an electron-attracting or electrondonating group and $R_6$ represents a hydrogen atom or a hydrocarbon radical, with the proviso that if one of Y and Z represents an acyl radical this can form a 5- or 6-membered saturated ring with $R_6$, onto the 4 carbon of a buta-1,3-diene carrying a hydrocarbon substitutent R on the 2 carbon that is to say the butadiene of the formula:

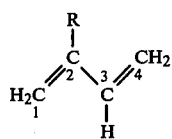

In fact, these compounds are of real industrial and economic value as they are used as precursors of intermediates for the synthesis of vitamins and perfumes.

I have found that the use of the process described in French Specification No. 2,366,237 and U.K. Patent Specification No. 1,553,002 cannot be applied directly to the preparation of these addition compounds. In fact, I have found that, in the case of the reaction of compounds I and II, since the diene is not symmetrical, four compounds are formed, corresponding to addition onto the four butadiene carbons, if one of palladium, nickel, platinum and cobalt is used as the transition metal. A mixture of the following compounds is thus obtained:

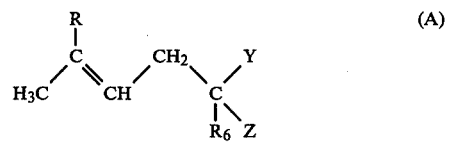

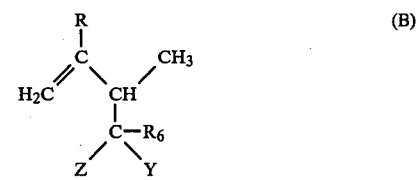

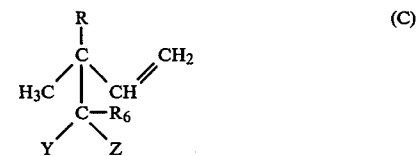

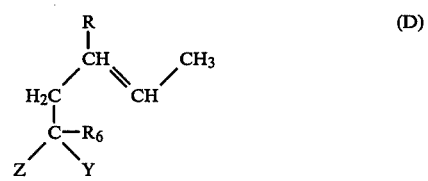

Furthermore, it is apparent from the experiments carried out that the larger the substituent R, the smaller the amount of products A, B, C and D formed, when the transition metals palladium, nickel, platinum and cobalt are used. Thus, if the compound of the formula (I) is myrcene, a very small amount of product is formed, and this makes the process totally unsuitable for industrial exploitation. However, if the yield is higher, the separation of the reaction products is difficult, lengthy and expensive.

It has now been found that, if it is desired to react compound I with compound II, only the use of rhodium as the transition metal makes it possible to obtain a totally selective addition onto the 4 carbon of butadiene, regardless of the size of the hydrocarbon substituent R, and a very considerably improved activity, compared with palladium, nickel, platinum and cobalt. The present invention thus permits the selective preparation of a compound under very advantageous technical and economic conditions.

The present invention therefore provides a process for the selective addition of a compound having an activated carbon onto the carbon atom in the 4-position of a buta-1,3-diene carrying a hydrocarbon substituent on the carbon atom in the 2-position, which process comprises reacting the compound having the activated carbon with the butadiene carrying the hydrocarbon substituent in water or in an aqueous-alcohol containing up to 50% by volume of an aliphatic alcohol containing 1 to 3 carbon atoms in the presence of a catalyst which consists of at least one water-soluble phosphine and at least one rhodium compound, the catalyst being in solution in the water or in the aqueous-alcohol.

It has been found that the use of the process in reacting a compound of the formula (I) with a compound of the formula (II) leads not only to the preparation of the above compound A, but also to the preparation of the following new compounds (A'):

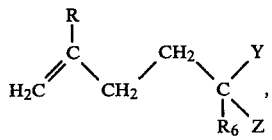
(A')

wherein R, $R_6$, Y and Z are as defined above, which is in itself very surprising. Mixtures of the compounds A and A' are formed. The invention thus also relates to the compounds A' and also to mixtures of the compounds A and A'.

The compounds A and A' can be used by themselves or in a mixture as precursors of intermediates for the synthesis of vitamins and perfumes.

More particularly, according to the invention, R in the formulae I, A and A' represents a hydrocarbon radical chosen from amongst the group comprising unsaturated or saturated aliphatic radicals, for example alkyl and alkenyl radicals, having from about 1 to 20 carbon atoms and phenyl and naphthyl radicals optionally substituted by one or more alkyl radicals having from 1 to 20 carbon atoms. $R_6$ represents a hydrogen atom or a hydrocarbon radical defined as for R above, it being possible for $R_6$ and R to be identical or different.

Examples of aliphatic radicals which may be mentioned are the radicals $C_nH_{2n+1}$, $C_nH_{2n-1}$, $C_nH_{2n-3}$ and $C_nH_{n-1}$, in which n is between about 1 and 20, such as —$CH_3$ (isoprene), —$C_2H_5$, —$C_4H_9$, —$C_8H_{17}$, —$C_{20}H_{41}$, —$C_4H_7$, —$C_6H_{11}$ (myrcene), —$C_8H_{15}$, —$C_{10}H_{19}$, —$C_8H_{13}$, —$C_{11}H_{19}$ ($\beta$-farnesene), —$C_2H$, —$C_4H_3$ and —$C_8H_7$, the common name of the most important compounds of the formula I being indicated in brackets. Examples of optionally substituted phenyl and naphthyl radicals which may be mentioned are tolyl, xylyl, 8-methylnaphth-1-yl and 5,8-dimethylnaphth-2-yl radicals.

More particularly, according to the invention, one of the symbols Y and Z in the formulae II, A' and A is chosen from amonst the electron-attracting group comprising the radicals of the formulae CHO, $COR_1$, $CO_2R_2$, $SO_2R_3$, $CONR_4R_5$, CN and $NO_2$, and the other is chosen from amongst the electron-attracting group defined above or the electron-donating group comprising the radicals of the formulae $NHCOR_7$, $OR_8$, OH, $OCOR_9$, $SR_{10}$ and SH, and halogen atoms, in which radicals $R_1$, $R_2$, $R_3$, $R_4$, $R_5$, $R_7$, $R_8$, $R_9$ and $R_{10}$ represent a hydrocarbon radical containing 1 to 12 carbon atoms. If Y and Z represent in one case an electron-attracting group and in the other an electron-donating group, they must be chosen so that the effect of the electron-attracting group is predominant.

The following compounds may be mentioned as examples of compounds II: pentane-2,4-dione, $CH_3COCH_2COCH_3$; butan-1-al-3-one, $CH_3COCH_2$-CHO; ethyl acetylacetate, $CH_3COCH_2COOC_2H_5$; methyl acetylcetate, $CH_3COCH_2COOCH_3$; phenylsulphonylacetone, $C_6H_5SO_2CH_2COCH_3$; ethyl phenylsulphonylcetate, $C_6H_5SO_2CH_2CO_2C_2H_5$; ethylsulphonylacetone, $C_2H_5SO_2CH_2COCH_3$; $CH_3COCH_2CON(CH_3)_2$; $CH_3COCH_2CON(CH_3)C_2H_5$; ethyl cyanoacetate, $NCCH_2CO_2C_2H_5$; cyanoacetone, $NCCH_2COCH_3$; ethyl nitroacetate, $NO_2CH_2CO_2C_2H_5$; nitroacetone, $NO_2CH_2COCH_3$; diethyl malonate, $CH_2(CO_2C_2H_5)_2$; hydroxyacetone, $HOCH_2COCH_3$; acetoin, $HOCH(CH_3)COCH_3$; and 2-ethoxycarbonylcyclohexanone.

The water-soluble phosphines which can be used within the scope of the present invention are those described in French Patent Specification No. 2,366,237.

More particularly, it is preferred to use at least one phosphine of the formula:

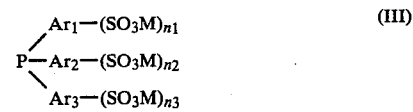
(III)

in which: $Ar_1$, $Ar_2$ and $Ar_3$, which are identical or different, each represent a radical chosen from amongst the group comprising phenylene and naphthylene radicals, these radicals being optionally substituted, M is a cationic radical of inorganic or organic origin, chosen so that the phosphine of the formula I is water-soluble, and $n_1$, $n_2$ and $n_3$, which are identical or different, are integers which are greater than or equal to 0 and less than or equal to 3, at least one of them being greater than or equal to 1.

The phenylene and naphthylene radicals can be substituted by any radicals which do not interfere with the solubility of the phosphine (III) in water. Examples of the latter radicals which may be mentioned are alkyl radicals having from 1 to 6 carbon atoms, alkoxy radicals having from 1 to 6 carbon atoms, halogen atoms, the radicals —OH, —CN, —$NO_2$ and -N-(alkyl)$_2$, and carboxylate radicals.

The process according to the invention is preferably carried out using at least one phosphine of the formula (III) in which $Ar_1$, $Ar_2$ and $Ar_3$, which are identical or different, each represent a radical chosen from amongst the group comprising the phenylene radical and substituted phenylene radicals.

Even more preferably, a phosphine in which at least one of the $SO_3M$ groups is in the meta-position on the benzene nucleus is used.

Preferably, M is chosen from amongst the group comprising the cations derived from the metals Na, K, Ca and Ba, $NH_4^+$ ions and quaternary ammonium ions such as tetramethylammonium, tetrapropylammonium and tetrabutylammonium ions.

$n_1$, $n_2$ and $n_3$ are preferably equal to 0 or 1, $n_1+n_2+n_3$ being between 1 and 3 ($1 \leq n_1+n_2+n_3 \leq 3$).

The compounds of the formula III which are more particularly preferred are the phosphines of the following formulae:

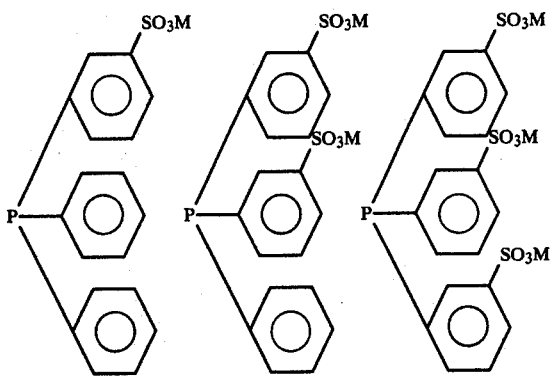

in which M has the above meaning.

The following compounds may be mentioned as other examples of phosphines (III) which can be used in the process according to the invention: the alkali metal or alkaline earth metal salts, the ammonium salts and the quaternary ammonium salts of (p-sulphophenyl)-diphenylphosphine, (m-sulpho-p-methylphenyl)-di-(p-methylphenyl)-phosphine, (m-sulpho-p-methoxyphenyl)-di-(p-methoxyphenyl)-phosphine, (m-sulpho-p-chlorophenyl)-di-(p-chlorophenyl)-phosphine, di-(p-sulphophenyl)-phenylphosphine, di-(m-sulpho-p-methylphenyl)-(p-methylphenyl)-phosphine, di-(m-sulpho-p-methoxyphenyl)-(p-methoxyphenyl)-phospine, di-(m-sulpho-p-chlorophenyl)-(p-chlorophenyl)-phosphine, tri-(p-sulphophenyl)-phosphine, tri-(m-sulpho-p-methylphenyl)-phosphine, tri-(m-sulpho-p-methoxyphenyl)-phosphine, tri-(m-sulpho-p-methoxyphenyl)-phosphine, tri-(m-sulpho-p-chlorophenyl)-phosphine, (o-sulpho-p-methylphenyl)-(m-sulpho-p-methylphenyl)-(m,m'-disulpho-p-methylphenyl)-phosphine and (m-sulphophenyl)-(m-sulpho-p-chlorophenyl)-(m,m'-disulpho-p-chlorophenyl)-phosphine.

The rhodium compound used must be water-soluble or capable of passing into solution in water, under the reaction conditions, by means of a coordination reaction with the water-soluble phosphines. The radical bonded to the metal is not critical provided that it satisfies these conditions.

According to a preferred embodiment of the process, the rhodium derivative is chosen from amongst the group comprising inorganic rhodium salts, organic rhodium salts and rhodium complexes, such as, for example, $RhCl_3$, $RhBr_3$, $Rh_2O$, $Rh_2O_3$, $Rh(NO_3)_3$, $Rh(CH_3COO)_3$, $Rh(CH_3COCHCOCH_3)_3$, $[RhCl(cycloocta-1,5-diene)]_2$, $[RhCl(CO)_2]_2$ and $RhCl_3(C_2H_5NH_2)_3$.

The use of $RhCl_3$ and $[RhCl(cycloocta-1,5-diene)]_2$ is very particularly preferred.

The amount of rhodium or of rhodium compound used is such that the number of gram atoms of elementary rhodium per litre of reaction solution is between about $10^{-4}$ and about 1. Preferably, it is between about 0.001 and 0.5.

To carry out the process satisfactorily, the amount of phosphine is chosen so that the number of gram atoms of trivalent phosphorus per gram atom of rhodium is between about 0.1 and about 200. Preferably, this number is between about 3 and about 100.

Although it is not essential, it is possible to add a rhodium reducer to the reaction medium. This reducer, which can be organic or inorganic, is used for the purpose of activating the formation of an active catalytic species in certain cases.

Examples which may be mentioned of reducers which can be used are sodium borohydride, zinc powder, potassium borohydride, magnesium and hydrazine. This reducer is added in an amount such that the number of redox equivalents is preferably between 1 and 10.

According to a particular but not obligatory embodiment of the invention, a base is added to the reaction medium for the purpose of improving the reactivity. Examples of particularly suitable bases which may be mentioned are alkali metal and alkaline earth metal hydroxides, carbonates and bicarbonates and aliphatic or aromatic tertiary amines. It is preferred to use between 0.005 and 5 mols of base/liter of aqueous solution.

The temperature at which the reaction is carried out can vary within wide limits. Preferably, the reaction is carried out at moderate temperatures below 200° C. More particularly, the temperature is between about 50° C. and 125° C.

The molar ratio of the compound II to the compound I is not critical. It is preferred to carry out the reaction with a slight molar excess of compound II (the compound having an activated carbon atom).

The minimum amount of water required is that which is sufficient to dissolve all the catalyst and at least part of the reactants I and II, the reaction taking place in the aqueous phase and the reaction products being in the water-immiscible organic phase.

In order to increase the reaction kinetics and facilitate the recycling of the catalyst, it is possible to carry out the reaction in the presence of a co-solvent. More particularly, some of the water required to carry out the reaction is replaced by an equivalent amount of an aliphatic alcohol containing 1 to 3 carbon atoms, such as methanol, ethanol or isopropanol. The amount of water which can be replaced is at most equal to half the amount of water required for carrying out the reaction without a co-solvent.

A practical method of carrying out the process of the invention consists in introducing, into a suitable reactor which has been purged with the aid of an inert gas (nitrogen or argon), either the aqueous or aqueous-alcoholic catalyst solution formed beforehand, or the various components, namely the phosphine, the water, if appropriate the alcohol, such as methanol, ethanol or isopropanol, the rhodium compound and, if appropriate, the reducer and the base. The reactor is heated to the reaction temperature before or after the introduction of the compound having an activated carbon atom, which can itself be introduced before, after or simultaneously with the substituted butadiene.

After the reaction has stopped, the reactor is cooled to ambient temperature. The contents of the reactor are drawn off and the reaction product, which is in the organic phase, is then isolated by separating the latter from the aqueous phase containing the catalyst, by decantation and, if appropriate, by extraction with the aid of a suitable solvent.

The residual aqueous or aqueous-alcoholic solution can be recycled into the reactor in order to catalyse a further reaction. In particular, in aqueous-methanolic solution, the catalyst can be recycled more than 25 times without loss of activity. The aqueous or aqueous-alcoholic solution can also remain in the reactor, in which case the organic products are drawn off after decantation.

The process according to the invention makes it possible to obtain selectivities of the order of 100% with respect to the compounds A and A'. These two compounds can be separated by any means known to those skilled in the art, such as, for example, by distillation.

The products of the general formula A' obtained in accordance with the process of the present invention are new products which can be isomerised to the product of the general formula A, in particular by operating under the conditions in French Pat. No. 70/07,199, published under No. 2,031,335. Generally, this isomerisation can be carried out by operating at a temperature of the order of 25° C., in the presence of a catalyst such as palladium-on-charcoal.

The following examples will reveal further characteristics and advantages of the invention. They cannot be considered as limiting the invention in any way.

EXAMPLES 1 TO 11:

Addition of pentane-2,4-dione onto isoprene in order to obtain

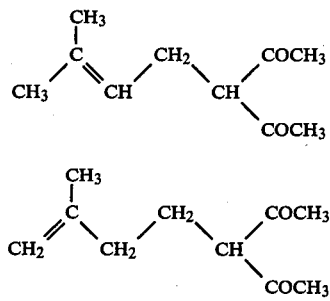

EXAMPLE 1

68.4 mg of [RhCl(cycloocta-1,5-diene)]$_2$, that is to say 0.27 milligram atom of rhodium, 0.30 g of:

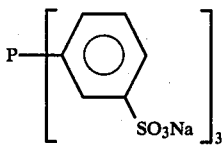

(which will be referred to as Na TPPTS in the following examples), that is to say 0.44 milligram atom of P$^{3+}$, 0.15 g (1.4 millimols) of Na$_2$CO$_3$ and 10 cm$^3$ of H$_2$O are introduced into a stainless steel autoclave purged with argon beforehand. 32 millimols (2.18 g) of isoprene and 38 millimols (3.8 g) of pentane-2,4-dione are then introduced.

The autoclave is heated at 80° C. for 6.5 hours, whilst stirring. After cooling, the contents of the autoclave are transferred into a separating funnel, in which an aqueous phase and an organic phase separate out. The aqueous phase collected, which is deep red in colour, contains the catalyst, and the colourless, catalyst-free, upper organic phase contains the following, according to analysis by NMR, mass spectrography and IR and determination by gas phase chromatography:

2.49 g of a' and
2.26 g of a,
which corresponds to a degree of conversion of the isoprene of 89.4% and a degree of conversion of the pentane-2,4-dione of 74.8%. The selectivity with respect to a+a' is 99%, relative to each reactant.

EXAMPLE 2

By following the procedure of Example 1, but using only 35.2 mg of [RhCl(cycloocta-1,5-diene)]$_2$, that is to say 0.14 milligram atom of rhodium, the following are obtained at the end of the reaction:

2.57 g of a' and
2.25 g of a,
which corresponds to a degree of conversion of the isoprene of 91.5% and to a degree of conversion of the pentane-2,4-dione of 76.3%, and the selectivity with respect to a+a' is 99%, relative to each reactant.

Comparison experiment

The above procedure is followed, by PdCl$_2$ (25 mg, that is to say 0.14 milligram atom of palladium) is used in place of [RhCl(cycloocta-1,5-diene)]$_2$.

The following are obtained:
0 g of a'
1.83 g of a
0.142 g of compound from addition onto the 1 carbon
0.163 g of compound from addition onto the 2 carbon
0.035 g of compound from addition onto the 3 carbon
and Qp 0.173 g of heavy products, that is to say a degree of conversion of the isoprene of 41.5% and a degree of conversion of the pentanedione of 33.9%, the selectivity with respect to a being 79%.

EXAMPLE 3

The procedure of Example 1 is followed, but 37.2 mg of [RhCl(cycloocta-1,5-diene)]$_2$, that is to say 0.15 milligram atom of rhodium, 60.3 millimols (4.1 g) of isoprene and 76.9 millimols (7.7 g) of pentane-2,4-dione are used.

The following are obtained:
5.12 g of a' and
4 g of a,
that is to say a degree of conversion of the isoprene of 90.7% and a degree of conversion of the pentane-2,4-dione of 70.9%, the selectivity with respect to a+a' being 98%.

EXAMPLE 4

The procedure of Example 1 is followed, but 49.6 mg of hydrated RhCl$_3$, that is to say 0.14 milligram atom of rhodium, are used.

The following are obtained:
2.4 g of a' and
1.85 g of a,
that is to say a degree of conversion of the isoprene of 80.8% and a degree of conversion of the pentane-2,4-dione of 65.4%, the selectivity with respect to a+a' being 99%.

EXAMPLE 5

The procedure of Example 1 is followed, but 10.8 mg of [RhCl(cycloocta-1,5-diene)]$_2$, that is to say 0.044 milligram atom of Rh, and 99.6 mg of Na TPPTS, that is to say 1.47 milligram atoms of P$^{3+}$, are used.

The following are obtained:
2.26 g of a' and
1.78 of g of a,
that is to say a degree of conversion of the isoprene of 76.7% and a degree of conversion of the pentane-2,4-dione of 60.7%, the selectivity with respect to a+a' being 99%.

EXAMPLE 6

The procedure of Example 5 is followed, but the reaction is carried out for 3 hours instead of 6.5 hours.

The following are obtained:
0.5 g of a' and
0.45 g of a,
that is to say a degree of conversion of the isoprene of 21% and a degree of conversion of the pentane-2,4-dione of 16%, the selectivity with respect to a+a' being 98.3%.

EXAMPLE 7

The procedure of Example 6 is followed, but the temperature is increased to 100° C.

The following are obtained:
2.36 g of a' and
2.14 g of a,
that is to say a degree of conversion of the isoprene of 85.9% and a degree of conversion of the pentane-2,4-dione of 70.1%, the selectivity with respect to a+a' being 98%.

EXAMPLE 8

The procedure of Example 5 is followed, but 330 mg of Na TPPTS, that is to say 0.50 milligram atom of $P^{3+}$, are used.

The following are obtained:
2.12 g of a' and
1.82 g of a,
that is to say a degree of conversion of the isoprene of 76.4% and a degree of conversion of the pentane-2,4-dione of 61.1%, the selectivity with respect to a+a' being 99%.

EXAMPLE 9

The procedure of Example 7 is followed, but without using $Na_2CO_3$.

The following are obtained:
0.39 g of a' and
0.37 g of a,
that is to say a degree of conversion of the isoprene of 14.3% and a degree of conversion of the pentane-2,4-dione of 11.6%, the selectivity with respect to a+a' being 100%.

EXAMPLE 10

The procedure of Example 1 is followed, but 10.8 mg of [RhCl(cycloocta-1,5-diene)]$_2$, that is to say 0.044 milligram atom of Rh, 100 mg of Na TPPTS, that is to say 0.148 milligram atom of $P^{3+}$, 20 cm$^3$ of $H_2O$, 64.1 millimols (4.36 g) of isoprene and 76 millimols (7.60 g) of pentane-2,4-dione are used.

The following are obtained:
1.78 g of a' and
1.46 g of a,
that is to say a degree of conversion of the isoprene of 31.5% and a degree of conversion of the pentanedione of 25.1%, the selectivity with respect to a+a' being 100%.

EXAMPLE 11

The procedure of Example 10 is followed, but 10 cm$^3$ of water are used and the autoclave is heated at 120° C. for 2 hours.

The following are obtained:
3.46 g of a' and
3.11 g of a,
that is to say a degree of conversion of the isoprene of 65.5% and a degree of conversion of the pentane-2,4-dione of 50.6%, the selectivity with respect to a+a' being 98.5%.

EXAMPLES 12 AND 13

Addition of ethyl acetylacetate onto isoprene in order to obtain:

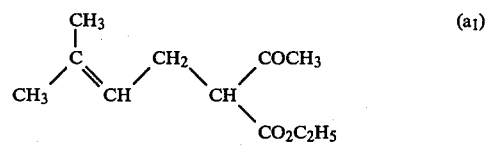
(a$_1$)

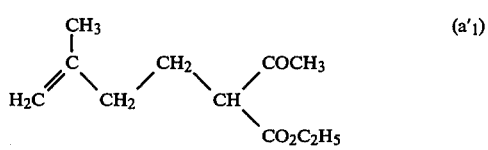
(a'$_1$)

EXAMPLE 12

33.7 mg of [RhCl(cycloocta-1,5-diene)]$_2$ (0.14 milligram atom of rhodium), 0.3 g of Na TPPTS (0.44 milligram atom of $P^{3+}$), 76 mg of $Na_2CO_3$ (0.72 millimol) and 30 cm$^3$ of $H_2O$ are introduced into a stainless steel autoclave purged with argon beforehand. 102.3 millimols of isoprene (6.9 g) and 125 millimols of ethyl acetylacetate (16.2 g) are then introduced. The autoclave is heated at 100° C. for 3 hours, whilst stirring.

The following are obtained:
6.21 g of a$_1$ and
11.9 g of a'$_1$,
that is to say a degree of conversion of the isoprene of 90.4% and a degree of conversion of the ethyl acetylacetate of 73.7%, the selectivity with respect to a$_1$+a'$_1$ being 99%.

EXAMPLE 13

The procedure of Example 12 is followed, using 132 mg of [RhCl(cycloocta-1,5-diene)]$_2$ (0.53 milligram atom), 1.21 g of Na TPPTS (1.79 milligram atom of $P^{3+}$), 0.75 g of $Na_2CO_3$ (7.1 millimols), 120 cm$^3$ of $H_2O$, 0.77 mol of isoprene (52.4 g) and 0.88 mol of ethyl acetylacetate (114 g).

The following are obtained:
38.6 g of a$_1$ and
81.2 g of a'$_1$,
that is to say a degree of conversion of the isoprene of 79.8% and a degree of conversion of the ethyl acetylacetate of 69%, the selectivity with respect to a$_1$+a'$_1$ being 99%.

EXAMPLE 14

Addition of phenylsulphonylacetone onto isoprene in order to obtain:

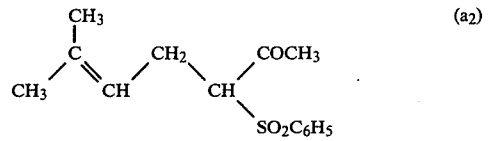
(a$_2$)

-continued

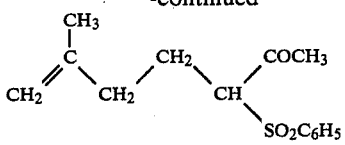
(a'2)

36.6 mg of [RhCl(cycloocta-1,5-diene)]$_2$ (0.15 milligram atom of rhodium), 0.32 g of Na TPPTS (0.47 milligram atom of P$^{3+}$), 0.15 g of Na$_2$CO$_3$ (0.4 millimol) and 10 cm$^3$ of H$_2$O are introduced into a stainless steel autoclave purged with argon beforehand. 33.2 millimols of isoprene (2.25 g) and 40 millimols of phenylsulphonylacetone (7.9 g) are then introduced.

The autoclave is heated at 100° C. for 3 hours, whilst stirring.

The following are obtained:
3.89 g of a$_2$ and
4.76 g of a'$_2$,
that is to say a degree of conversion of the isoprene of 97.9% and a degree of conversion of the phenylsulphonylacetone of 81.3%, the selectivity with respect to a$_2$+a'$_2$ being 99%.

EXAMPLES 15 TO 17

Addition of pentane-2,4-dione onto myrcene in order to obtain:

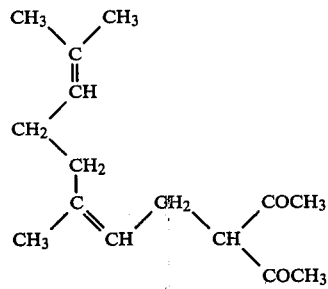
(a$_3$)

and

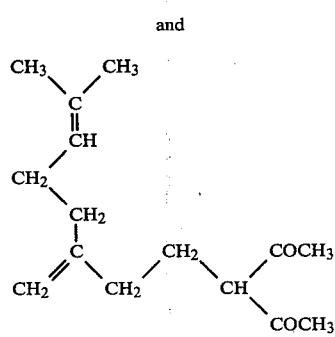
(a'$_3$)

EXAMPLE 15

39.1 mg of [RhCl(cycloocta-1,5-diene)]$_2$ (0.16 milligram atom of rhodium), 0.33 g of Na TPPTS (0.49 milligram atom of P$^{3+}$), 0.15 g of Na$_2$CO$_3$ (1.4 millimols) and 10 cm$^3$ of H$_2$O are introduced into a stainless steel autoclave purged with argon beforehand.

24.6 millimols of myrcene (3.34 g) and 38.8 millimols of pentane-2,4-dione (3.9 g) are then introduced.

The autoclave is heated at 80° C. for 24 hours, whilst stirring.

3.19 g of a$_3$+a'$_3$ (equimolar mixture) are obtained, that is to say a degree of conversion of the myrcene of 55.5% and a degree of conversion of the pentane-2,4-dione of 35.2%, the selectivity with respect to a$_3$+a'$_3$ being 98.5%.

Comparison experiment

By following the above procedure, but using 24 mg of PdCl$_2$ (0.14 miligram atom of palladium) instead of the [RhCl(cycloocta-1,5-diene)]$_2$, 1 g of an organic product essentially consisting of myrcene dimers is obtained after removal of the reactants which have not reacted. The presence of the compounds a$_3$ and a'$_3$ is not observed.

EXAMPLE 16

The procedure of Example 15 is followed, but the autoclave is heated at 120° C. for 3 hours.

3.8 g of a$_3$+a'$_3$ (equimolar mixture) are obtained.

The degree of conversion of the myrcene is 66.9% and that of the pentane-2,4-dione is 41.7%, the selectivity with respect to a$_3$+a'$_3$ being 98.5%.

EXAMPLE 17

The procedure of Example 15 is followed, but 1.06 g of Na TPPTS (1.57 milligram atoms of P$^{3+}$) are used and the autoclave is heated at 120° C. for 3 hours.

3.7 g of a$_3$+a'$_3$ (equimolar mixture) are obtained.

The degree of conversion of the myrcene is 63.1% and that of the pentane-2,4-dione is 39.7%, the selectivity with respect to a$_3$+a'$_3$ being 99%.

EXAMPLES 18 TO 22

Addition of ethyl acetylacetate onto myrcene in order to obtain:

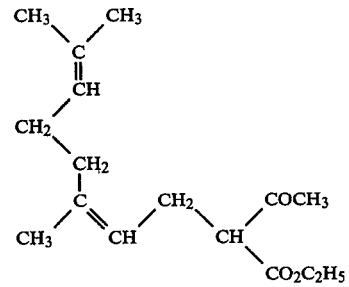
(a$_4$)

and

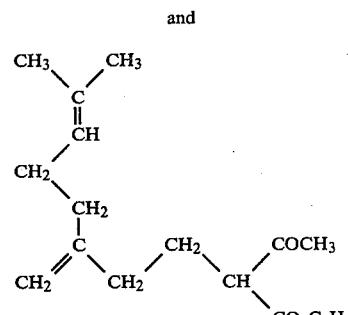
(a'$_4$)

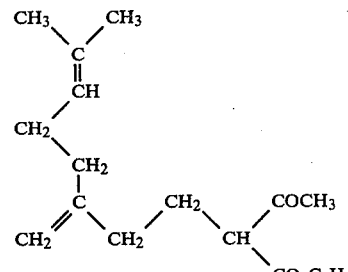

EXAMPLE 18

100 mg of [RhCl(cycloocta-1,5-diene)]$_2$ (0.41 milligram atom of rhodium), 0.78 g of Na TPPTS (1.15 milligram atom of P$^{3+}$), 0.156 g of Na$_2$CO$_3$ (1.5 millimols) and 30 cm$^3$ of H$_2$O are introduced into a stainless steel autoclave purged with argon beforehand.

64.7 millimols of myrcene (8.8 g) and 127 millimols of ethyl acetylacetate (16.5g) are then introduced.

The autoclave is heated at 100° C. for 6 hours, whilst stirring. 12.66 g of $a_4+a'_4$ (equimolar mixture) are obtained.

The degree of conversion of the myrcene is 80% and that of the ethyl acetylacetate is 40%, the selectivity with respect to $a_4+a'_4$ being 99%.

EXAMPLE 19

The procedure of Example 18 is followed, but 49 mg of [RhCl(cycloocta-1,5-diene)]$_2$ (0.2 milligram atom of rhodium), 1.42 g of Na TPPTS (2.1 milligram atoms of $P^{3+}$), 70 mg of $Na_2CO_3$ (0.65 millimol), 30 cm$^3$ of $H_2O$, 82 millimols of myrcene (11.15 g) and 117 millimols of ethyl acetylacetate (15.2 g) are used.

The autoclave is heated at 150° C. for 1 hour, whilst stirring.

6.07 g of $a_4+a'_4$ (equimolar mixture) are obtained.

The degree of conversion of the myrcene is 33% and that of the ethyl acetylacetate is 23.2%, the selectivity being 99%.

EXAMPLE 20

Addition of phenylsulphonylacetone onto myrcene in order to obtain:

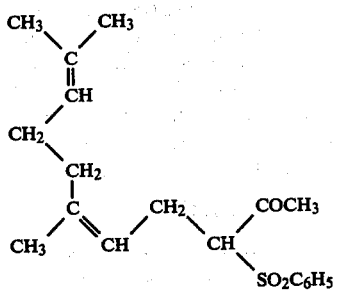
(a$_5$)

and

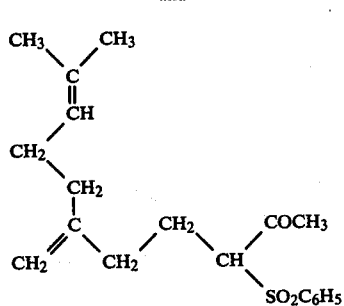
(a'$_5$)

67.6 mg of [RhCl(cycloocta-1,5-diene)]$_2$ (0.27 milligram atom of rhodium), 0.64 g of Na TPPTS (0.95 milligram atom of $P^{3+}$), 0.30 g of $Na_2CO_3$ (2.8 millimols) and 20 cm$^3$ of $H_2O$ are introduced into a stainless steel autoclave purged with argon beforehand. 81.2 millimols of myrcene (11.05 g) and 80 millimols of phenylsulphonylacetone (15.84 g) are then introduced.

The autoclave is heated at 100° C. for 6 hours, whilst stirring.

The following are obtained:
8.2 g of $a_5$ and
10.01 g of $a'_5$,
that is to say a degree of conversion of the myrcene of 67.1% and a degree of conversion of the phenylsulphonylacetone of 68.1%, the selectivity with respect to $a_5+a'_5$ being 99%.

EXAMPLE 21

Addition of ethyl acetylacetate onto β-farnesene in order to obtain:

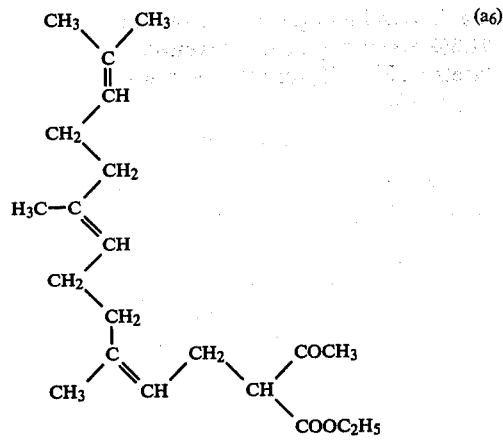

and

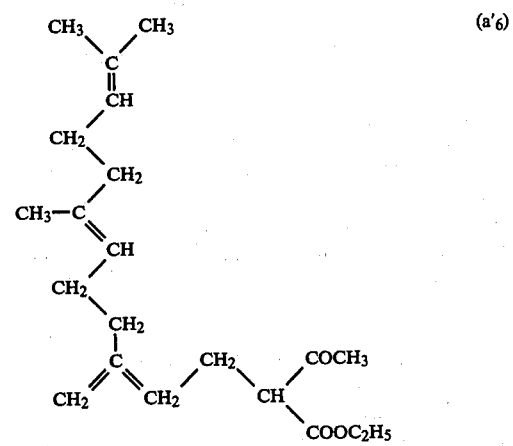

64 mg of [RhCl(cycloocta-1,5-diene)]$_2$ (0.26 milligram atom of rhodium), 0.53 g of Na TPPTS (0.78 milligram atom of $P^{3+}$), 0.20 g of $Na_2CO_3$ (1.9 millimols) and 15 cm$^3$ of $H_2O$ are introduced into a stainless steel autoclave purged with argon beforehand.

16 millimols of β-farnesene (3.26 g) and 58.9 millimols of ethyl acetylacetate (7.66 g) are then introduced.

The autoclave is heated at 120° C. for 6 hours, whilst stirring.

2.34 g of $a_6+a'_6$ (equimolar mixture) are obtained.

The degree of conversion of the β-farnesene is 43.7% and that of the ethyl acetylacetate is 11.9%, the selectivity with respect to $a_6+a'_6$ being 99%.

EXAMPLE 22

Addition of isoprene onto ethyl acetylacetate in order to obtain $a_1$ and $a'_1$.

41.6 mg of [RhCl(cycloocta-1,5-diene)]$_2$ (0.17 milligram atom of rhodium), 0.58 g of Na TPPTS (0.86 milligram atom of $P^{3+}$), 0.44 g of triethylamine, $N(C_2H_5)_3$ (4.35 millimols) and 30 cm$^3$ of $H_2O$ are introduced into a stainless steel autoclave purged with argon beforehand.

99.8 millimols of isoprene (6.78 g) and 126 millimols of ethyl acetylacetate (16.38 g) are then introduced.

The autoclave is heated at 100° C. for 3 hours, whilst stirring.

The following are obtained:
6.05 g of $a_1$ and
12.50 g of $a'_1$,
that is to say a degree of conversion of the isoprene of 94.8% and a degree of conversion of the ethyl acetylacetate of 75.1%, the selectivity with respect to $a_1+a'_1$ being 99%.

EXAMPLE 23

Addition of isoprene onto 2-ethoxycarbonylcyclohexanone in order to obtain:

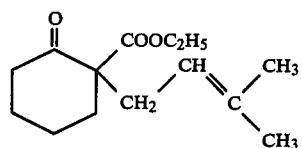

$a_7$

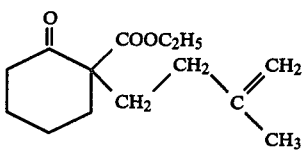

$a'_7$ 66 mg of [RhCl(cycloocta-1,5-diene)]$_2$, that is to say 0.26 milligram atom of rhodium, 0.85 g of Na TPPTS (1.33 milligram atoms of $P^{3+}$), 0.24 g of $NA_2CO_3$ (2.26 millimols) and 15 cm$^3$ of water are introduced into a stainless steel autoclave purged with argon beforehand. 81.5 millimols of isoprene (5.55 g) and 92.9 millimols of 2-ethoxycarbonylcyclohexanone (15.81 g) are then introduced.

The autoclave is heated at 100° C. for 3 hours, whilst stirring. The following are obtained:
4.9 g of $a_7$ and
4.95 g of $a'_7$,
that is to say a degree of conversion of the isoprene of 50.7% and a degree of conversion of the 2-ethoxycarbonylcyclohexanone of 44.5%, the selectivity with respect to $a_7+a'_7$ being 99%.

EXAMPLE 24

Addition of hydroxyacetone onto isoprene in order to obtain:

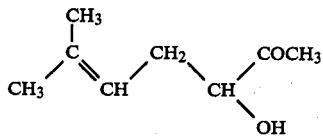

($a_8$)

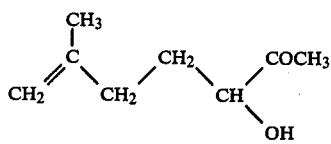

($a'_8$)

66 mg of [RhCl(cycloocta-1,5-diene)]$_2$, that is to say 0.26 milligram atom of rhodium, 0.90 g of Na TPPTS (1.34 milligram atoms of $P^{3+}$), 0.25 g of $Na_2CO_3$ (2.38 millimols) and 15 cm$^3$ of water are introduced into a stainless steel autoclave purged with argon beforehand. 104.7 millimols of isoprene (7.13 g) and 128 millimols of hydroxyacetone (9.49 g) are then introduced. The autoclave is heated at 100° C. for 16 hours, whilst stirring.

1.77 g of a product containing 70% of an equimolecular mixture of $a_8+a'_8$ are obtained (that is to say a degree of conversion of the isoprene of 10%).

EXAMPLE 25

Addition of acetoin onto isoprene in order to obtain:

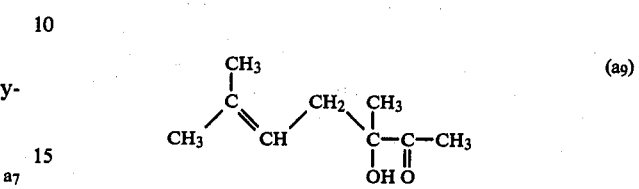

($a_9$)

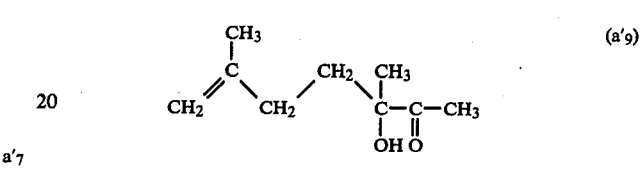

($a'_9$)

64.8 mg of [RhCl(cycloocta-1,5-diene)]$_2$, that is to say 0.26 milligram atom of rhodium, 0.90 g of Na TPPTS (1.34 milligram atoms of $P^{3+}$), 0.25 of $Na_2CO_3$ (2.36 millimols), 11 g of acetoin (124.8 millimols) and 15 cm$^3$ of water are introduced into a stainless steel autoclave purged with argon beforehand. 103.8 millimols of isoprene (7.07 g) are then introduced and the autoclave is heated at 100° C. for 16 hours, whilst stirring.

3.18 g of $a_9+a'_9$ are obtained, that is to say a degree of conversion of the isoprene of 19.6%.

EXAMPLE 26

Influence of an alcohol on the addition of methyl acetylacetate onto myrcene in order to obtain:

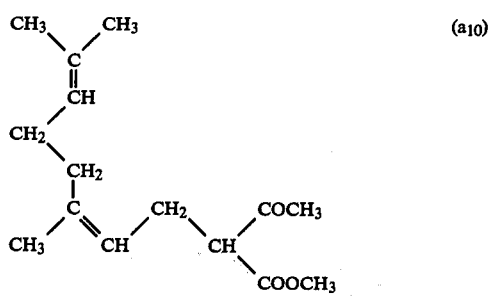

($a_{10}$)

and

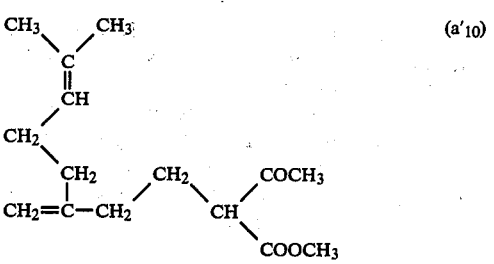

($a'_{10}$)

(a) without methanol 41.1 mg of [RhCl(cycloocta-1,5-diene)]$_2$ (0.167 milligram atom of rhodium), 2.2 g of Na TPPTS (3.256 milligram atoms of $P^{3+}$), 72 mg of $Na_2CO_3$ (0.68 millimol) and 20 cm$^3$ of water are introduced into a stainless steel reactor purged with argon beforehand.

117 millimols of myrcene (15.92 g) and 120 millimols of methyl acetylacetate (13.9 g) are then introduced.

The autoclave is heated at 90° C. for 1 hour, whilst stirring.

7.376 g of an equimolecular mixture of $a_{10}+a'_{10}$ are obtained. The degree of conversion of the myrcene is 24.9% and that of the methyl acetylacetate is 24.4%, the selectivity with respect to $a_{10}+a'_{10}$ being 99%.

(b) with methanol 40.8 mg of [RhCl(cycloocta-1,5-diene)]$_2$ (0.165 milligram atom of rhodium), 2.2 g of Na TPPTS (3.256 milligram atoms of $P^{3+}$), 78.2 mg of Na$_2$CO$_3$ (0.68 millimol), 15 cm$^3$ of water and 5 cm$^3$ of methanol are introduced into a stainless steel reactor purged with argon beforehand.

117 millimols of myrcene (15.92 g) and 120 millimols of methyl acetylacetate (13.9 g) are then introduced.

The autoclave is heated at 90° C. for 1 hour, whilst stirring.

12.488 g of an equimolecular mixture of $a_{10}+a'_{10}$ are obtained. The degree of conversion of the myrcene is 42.4% and that of the methyl acetylacetate is 41.3%, the selectivity with respect to $a_{10}+a'_{10}$ being 99%.

I claim:

1. In a process for the preparation of compounds of the formulae:

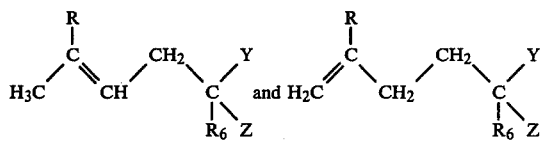

in which R is selected from the group consisting of saturated or unsaturated aliphatic radicals having from about 1 to 20 carbon atoms, and phenyl and naphthyl radicals unsubstituted or substituted by one or more alkyl radicals having from 1 to 20 carbon atoms, R$_6$ represents a hydrogen atom or a hydrocarbon radical, one of Y and Z represents an electron-attracting group and the other of Y and Z represents an electron-attracting or electron-donating group, with the proviso that if one of Y and Z represents an acyl radical, this can form a 5- or 6-membered saturated ring with R$_6$, by the reaction of a compound having an activated carbon of the formula:

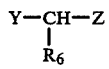

in which R$_6$, Y and Z are as hereinbefore defined, with a buta-1,3-diene carrying a hydrocarbon substituent on the carbon atom in the 2-position of the formula:

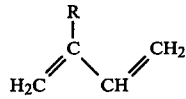

is which R is as hereinbefore defined, in the presence of a catalyst, the improvement which consists in carrying out the said reaction in water or in an aqueous-alcohol containing up to 50% by volume of an aliphatic alcohol containing 1 to 3 carbon atoms in the presence of a catalyst which consists of at least one water-soluble phosphine and at least one rhodium compound, the catalyst being in solution in the water or in the aqueous-alcohol.

2. Process according to claim 1, in which the rhodium compound is selected from the group consisting of inorganic rhodium salts, organic rhodium salts and rhodium complexes.

3. Process according to claim 2, in which the rhodium compound is selected from the group consisting of RhCl$_3$, RhBr$_3$, Rh$_2$O, Rh$_2$O$_3$, Rh(NO$_3$)$_3$, Rh(CH$_3$COO)$_3$, Rh(CH$_3$COCHCOCH$_3$)$_3$, [RhCl(cycloocta-1,5-diene)]$_2$, [RhCl(CO)$_2$]$_2$ and RhCl$_3$(C$_2$H$_5$NH$_2$)$_3$.

4. Process according to claim 1, in which the amount of rhodium compound used is such that the number of gram atoms of rhodium in said compound per liter of reaction solution is between about $10^{-4}$ and about 1.

5. Process according to claim 4, in which the number of gram atoms of rhodium in said compound per liter of reaction solution is between about 0.001 and about 0.5.

6. Process according to claim 1, in which the amount of phosphine is such that the number of gram atoms of trivalent phosphorus per gram atom of rhodium is between about 0.1 and about 200.

7. Process according to claim 6, in which the number of gram atoms of trivalent phosphorus per gram atom of rhodium is between about 3 and about 100.

8. Process according to claim 1 in which R$_6$ is selected from the group consisting of saturated or unsaturated aliphatic radicals containing 1 to 20 carbon atoms, and phenyl and naphthyl radicals unsubstituted or substituted by one or more alkyl radicals containing 1 to 20 carbon atoms.

9. Process according to claim 1, in which the electron-attracting groups are selected from the group consisting of radicals of the formulae CHO, COR$_1$, CO$_2$R$_2$, SO$_2$R$_3$, CON(R$_4$R$_5$), CN and NO$_2$, and the electron-donating group is selected from the group consisting of radicals of the formulae NHCOR$_7$, OR$_8$, OH, OCOR$_9$, SR$_{10}$ and SH, and halogen atoms, in which radicals R$_1$, R$_2$, R$_3$, R$_4$, R$_5$, R$_7$, R$_8$, R$_9$ and R$_{10}$ each represent a hydrocarbon group containing 1 to 12 carbon atoms.

10. Process according to claim 1, in which a rhodium reducer is added to the reaction medium.

11. Process according to claim 1 in which a base is added to the reaction medium.

12. Process according to claim 1 in which the reaction temperature is below 200° C.

13. Process according to claim 1, in which R is an aliphatic radical having from 1 to 20 carbon atoms selected from the group consisting of $C_nH_{2n+1}$, $C_nH_{2n-1}$, $C_nH_{2n-3}$ and $C_nH_{n-1}$, in which n is between 1 and 20.

14. Process according to claim 1, in which the said buta-1,3-diene is selected from isoprene, myrcene or β-farnesene.

15. Process according to claim 1, in which the compound having an activated carbon is selected from pentane-2,4,-dione, methyl acetylacetate, ethyl acetylacetate, phenylsulphonylacetone, hydroxyacetone, acetoin or 2-ethoxy-carbonylcyclohexanone.

* * * * *